United States Patent [19]

Owen et al.

[11] Patent Number: 5,102,428

[45] Date of Patent: Apr. 7, 1992

[54] INTEGRATED PROCESS FOR THE PRODUCTION OF DIISOPROPYL ETHER AND GASOLINE

[75] Inventors: Hartley Owen, Belle Mead; Mohsen N. Harandi, Lawrenceville, both of N.J.

[73] Assignee: Mobil Oil Corporation, Fairfax, Va.

[21] Appl. No.: 424,421

[22] Filed: Oct. 20, 1989

[51] Int. Cl.⁵ .............................................. C10L 5/00
[52] U.S. Cl. ...................................... 44/448; 44/446; 568/695; 568/697; 568/698; 568/699
[58] Field of Search ............... 44/53, 56, 77; 568/697, 568/698, 699, 695; 585/310, 318, 639, 654, 655, 737, 738

[56] References Cited

U.S. PATENT DOCUMENTS

| | | | |
|---|---|---|---|
| 4,042,633 | 8/1977 | Woods | 260/614 R |
| 4,182,914 | 1/1980 | Imaizumi | 568/697 |
| 4,334,890 | 6/1982 | Kochar et al. | 44/53 |
| 4,393,250 | 7/1983 | Gottlieb et al. | 568/697 |
| 4,413,150 | 11/1983 | Briggs | 568/697 |
| 4,418,219 | 11/1983 | Hanes et al. | 568/697 |
| 4,423,251 | 12/1983 | Pujado et al. | 568/697 |
| 4,503,263 | 3/1985 | Olah | 568/694 |
| 4,544,776 | 10/1985 | Osterburg et al. | 568/697 |
| 4,647,703 | 3/1987 | Torck et al. | 568/697 |
| 4,664,675 | 5/1987 | Torck et al. | 44/53 |
| 4,665,237 | 5/1987 | Arakawa et al. | 568/697 |
| 4,714,787 | 11/1987 | Bell et al. | 568/697 |
| 4,827,045 | 5/1989 | Harandi et al. | 568/697 |
| 4,857,664 | 8/1989 | Huang et al. | 568/695 |

Primary Examiner—Margaret B. Medley
Attorney, Agent, or Firm—Alexander J. McKillop; Charles J. Speciale; L. G. Wise

[57] ABSTRACT

A process is disclosed for integrating etherification to produce diisopropyl ether (DIPE) with processes to convert oxygenates and hydrocarbons to gasoline boiling range hydrocarbons in a manner which eliminates the requirement to recycle unreacted $C_3$ hydrocarbons to the DIPE etherification zone. In the novel integrated process the unreacted $C_3$ hydrocarbons are separated as vapor and passed to a conversion zone in contact with acidic metallosilicate catalyst. Depending on the conversion conditions the unreacted $C_3$ hydrocarbons are converted to gasoline, distillate and/or aromatics, preferably in conjunction with additional feedstock containing lower oxygenates, olefins or paraffins. Also, isopropanol (IPA) and minor by-product dimers and trimers of propene from the DIPE reaction are separated and passed as a feedstream to the oxygenates and hydrocarbon conversion zone. In one embodiment, the water feedstream for the DIPE reactor is first passed to the DIPE effluent high pressure separator where it serves to extract a portion of the IPA in the effluent stream. The aqueous effluent from the high pressure separator is then introduced into the etherification zone for hydration of propene and etherification to form DIPE.

25 Claims, 2 Drawing Sheets

INTEGRATED PROCESS FOR THE PRODUCTION OF DIISOPROPYL ETHER AND GASOLINE

This invention relates to a novel method and means for integrating the production of gasoline boiling range hydrocarbons and diisopropyl ether (DIPE). More particularly, the invention relates to the integration of $C_3$ hydrocarbon hydration and etherification with processes for the conversion of oxygenates, olefins and paraffins to higher molecular weight hydrocarbons. The process incorporates improvements in the product recovery section design for DIPE enhancing product separation and etherification reactor operating conditions.

BACKGROUND OF THE INVENTION

Lower molecular weight alcohols and ethers such as isopropanol (IPA) and diisopropyl ether (DIPE) are in the gasoline boiling range and are known to have high blending octane numbers. In addition, by-product propylene from which IPA and DIPE can be made is usually available in a fuels refinery. An important aspect of research in the petroleum industry relates to processes to produce high octane gasolines blended with lower aliphatic alkyl ethers as octane boosters and supplementary fuels. $C_5$–$C_7$ methyl alkyl ethers, especially methyl tertiary butyl ether (MTBE) and tertiary amyl methyl ether (TAME) have been found particularly useful for enhancing gasoline octane, as has diisopropyl ether (DIPE). Improvements to the processes related to the production of these ethers are matters of high importance and substantial challenge to research workers in the petroleum refining arts.

The catalytic hydration of olefins, particularly $C_3$ and $C_4$ olefins, to provide alcohols and ethers is a well-established art and is of significant commercial importance. Representative olefin hydration processes are disclosed in U.S. Pat. Nos. 2,262,913; 2,477,380; 2,797,247; 3,798,097; 2,805,260; 2,830,090; 2,861,045; 2,891,999; 3,006,970; 3,198,752; 3,810,848; 3,989,762, among others.

The production of ether from secondary alcohols such as isopropanol and light olefins is known. As disclosed in U.S. Pat. No. 4,182,914, DIPE is produced from IPA and propylene in a series of operations employing a strongly acidic cation exchange resin as catalyst. Recently, processes for the hydration of olefins to provide alcohols and ethers using zeolite catalyst have been disclosed by Bell et al. in U.S. patent applications Ser. Nos. 336,582 filed Apr. 10, 1989; 336,504 filed Apr. 11, 1989; 139,569 filed Dec. 30, 1987; 265,324 to Wang et al. filed Oct. 27, 1988; and 139,566 (allowed) to Wang filed Feb. 30, 1987. These applications are incorporated herein in their entirety by reference.

In the conversion of a water feedstream and a $C_3$ hydrocarbons feedstream comprising propene and propane to DIPE and IPA, the conversion per pass is typically about 60%. Recycling of the unreacted $C_3$'s unavoidably involves compression and recycling of unreacted propene to the etherification reactor. This, in turn, requires feeding and operating the reactor at higher pressures in order to maintain an effective propene partial pressure in the vessel; a situation inimical to improved process economics. Also, separating IPA from the reaction effluent and recycling IPA to the etherification reactor as typically carried out presents additional process problems.

It is an object of the present invention to provide an integrated process to produce DIPE and gasoline boiling range hydrocarbons.

It is another object of the present invention to provide a process for the production of DIPE and gasoline boiling range hydrocarbons without recycling unreacted $C_3$ hydrocarbons.

Yet another object of the present invention is to provide an improved means for separating and recycling IPA in the DIPE process.

SUMMARY OF THE INVENTION

A process has been discovered for integrating etherification to produce DIPE with processes to convert oxygenates and hydrocarbons to gasoline boiling range hydrocarbons in a manner which eliminates the incentive to recycle unreacted $C_3$ hydrocarbons to the DIPE etherification zone. In the novel integrated process the unreacted $C_3$ hydrocarbons are separated as vapor and passed to a conversion zone in contact with acidic metallosilicate catalyst. Depending on the conversion conditions the unreacted $C_3$ hydrocarbons are converted to gasoline, distillate and/or aromatics, preferably in conjunction with additional feedstock containing lower oxygenates, olefins or paraffins. Also, IPA and by-product dimers and trimers of propene from the DIPE reaction are separated and passed as a feedstream to the oxygenates and hydrocarbon conversion zone. In one embodiment, the water feedstream for the DIPE reactor is first passed to the DIPE effluent high pressure separator where it serves to extract a portion of the IPA in the effluent stream. The aqueous effluent from the high pressure separator is then introduced into the etherification zone for hydration of propene and etherification to form DIPE.

More particularly, an integrated process has been discovered for the production of diisopropyl ether and gasoline boiling range hydrocarbons which comprises contacting $C_3$ hydrocarbon feedstock and the high pressure separator aqueous effluent recycle stream with acidic hydration and etherification catalyst in an etherification zone under etherification conditions to produce an effluent stream containing diisopropyl ether, isopropanol, unreacted water, unreacted $C_3$ hydrocarbons and higher olefinic hydrocarbons. The effluent stream is separated and extracted in a high pressure separator in contact with a fresh water feedstream to produce the aqueous effluent recycle stream which contains a portion of the isopropanol produced in the etherification zone. Another separator effluent stream contains diisopropyl ether, unextracted isopropanol, unreacted $C_3$ hydrocarbons and higher olefinic hydrocarbons. This stream is optionally heated and flashed at a temperature sufficient to further separate the separator effluent to produce a flash evaporator overhead vapor stream for compression and recycle to the etherification zone. The feed to the flash evaporator operates at a pressure slightly above that of the downstream recovery section and flash evaporator. The recycle stream contains a major portion of the unreacted $C_3$ hydrocarbons. An evaporator bottom stream containing diisopropyl ether, unextracted isopropanol, a minor portion of said unreacted $C_3$ hydrocarbons and higher olefinic hydrocarbons is sent to a recovery section where it is separated to produce diisopropyl ether, a first stream containing $C_3$ hydrocarbons and a second stream containing isopropanol and higher olefinic hydrocarbons. These first and second streams are introduced to an oxygenates and hydrocarbons conversion zone in contact with acidic metallosilicate catalyst particles under oxygenates and hydrocarbons conversion conditions whereby the evaporator bottom stream products comprising unreacted C$_3$ hydrocarbons, isopropanol and higher olefinic hydrocarbons are converted to high quality, higher molecular weight gasoline boiling range hydrocarbons. In a preferred embodiment the flash evaporator overhead stream is also passed to the conversion zone.

DETAIL DESCRIPTION OF THE INVENTION

Figure 1:
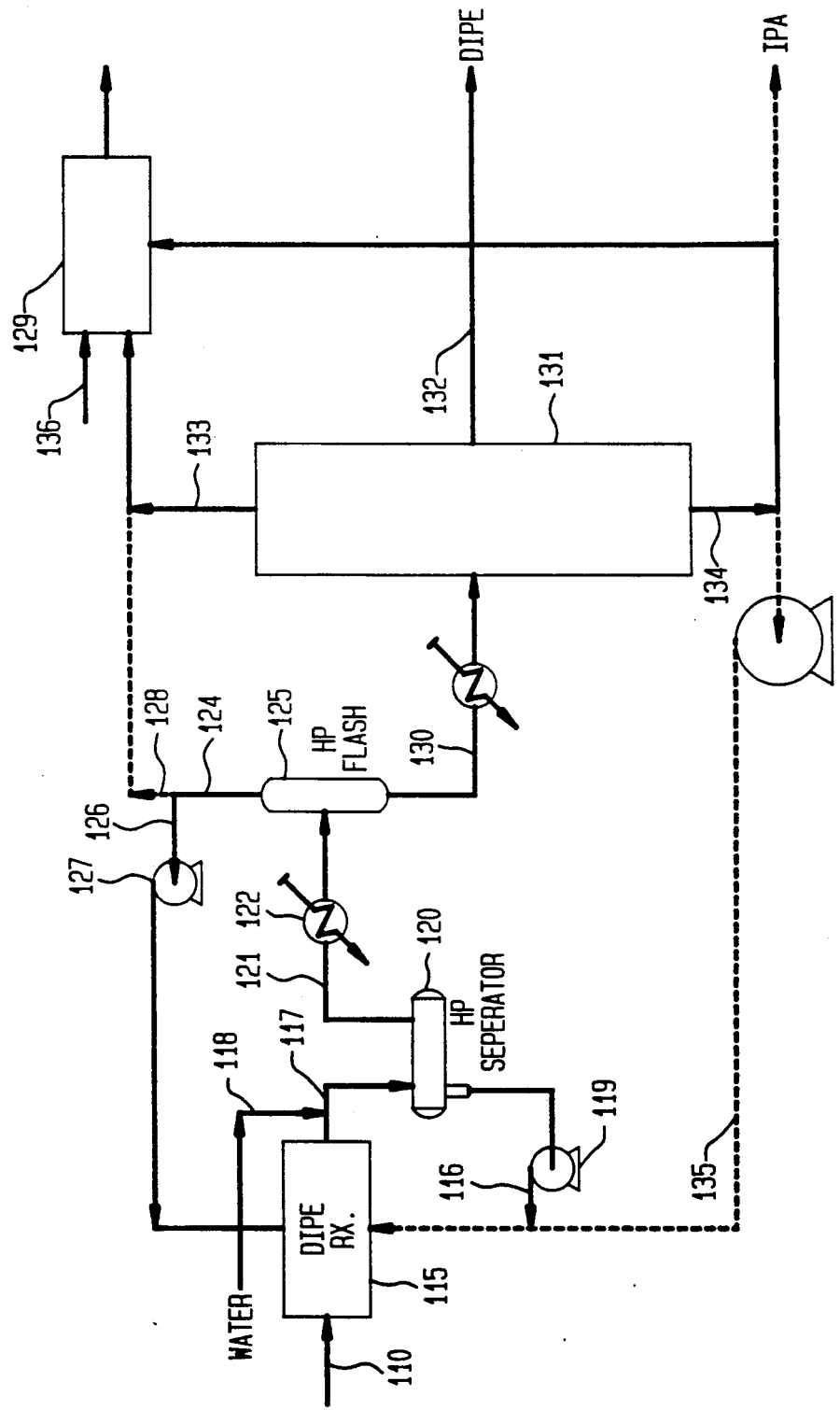
FIG. 1 is a process flow schematic illustrating the integrated process of the invention.

In one embodiment of the instant invention the principal components of known processes are integrated in a manner providing a highly advantageous and surprising advancement in refinery technology leading to the production of DIPE as well gasoline, distillate and/or aromatics. Known processes are combined in a unique configuration that provides enhancement of the performance of component processes, achieving surprising advantages for the integrated process. The processes integrated include C$_3$ olefins hydration to produce alcohols and ethers and olefins and/or oxygenates conversion over zeolite catalyst to produce gasoline (MOG-Mobil Olefins to Gasoline process), distillate (MOGD-Mobil Olefin to Gasoline and Distillate process) or aromatics (M-2 Forming-Mobil Aromatization process).

Various processes in the aforenoted field of oxygenates and/or olefins conversion technology are described in the following U.S. patents which are incorporated herein in their entirety by reference: U.S. Pat. Nos. 3,894,107 (Butter, et al); 3,928,483; 4,025,575; 4,252,479 (Chang, et al); 4,025,572 (Lago); 4,328,384 (Daviduk, et al); 4,547,616 (Avidan, et al); 4,450,311 (Right, et al); 3,960,978 and 4,021,502 (Plank, Rosinski and Givens); 4,150,062, 4,211,640 and 4,227,992 (Garwood, et al). Operating details for typical olefin oligomerization units are disclosed in U.S. Pat. Nos. 4,456,779; 4,497,968 (Owen et al.) and 4,433,185 (Tabak), incorporated herein by reference. Aromatization of hydrocarbons in contact with zeolite catalyst is described in U.S. Pat. No. 3,845,150 to Yan et al., also incorporated herein in entirety by reference, The term oxygenates or oxygenate as used herein comprises, individually or in combination, C$_1$-C$_8$ lower aliphatic, acyclic alcohols or alkanol and symmetrical or unsymmetrical C$_2$-C$_9$ ethers.

In the process to prepare DIPE a feedstock comprising propene or a refinery C$_3$ hydrocarbon stream comprising olefins and paraffins, i.e., propene and propane, is contacted at elevated pressure with an acidic catalyst and water as a reactant to hydrate propene to form isopropanol (IPA) and etherify IPA to DIPE. Minor amounts of addition products of propene are also formed in the acidic catalyst environment, particularly hexenes and nonenes. On a per pass basis, the conversion of propene generally is about 60%, or between 50% and 70%. The effluent from the hydration and etherification zone is conventionally passed to a high pressure separator wherein an aqueous stream is separated containing IPA and a stream that contains the unreacted C$_3$ hydrocarbons comprising propene and propane, if an olefin and paraffin feedstock has been used. In order to recover the unreacted C$_3$ hydrocarbons and recycle them to the etherification zone the temperature of the C$_3$ stream from the high pressure separator is raised and the stream is introduced to a flash evaporator under condition sufficient to separate a major portion of unreacted C$_3$ hydrocarbons. This recycle stream, typically containing both propene and propane, is recompressed and fed to the pressurized DIPE reactor. Since the recycle stream is rich in propane the DIPE feedstock stream pressure is increased in order to maintain the partial pressure of propene in the reactor. Conventionally, DIPE is recovered by distillation and/or extraction of the flash evaporator bottom stream. This recovery system also separates an IPA stream and light hydrocarbon stream such as a portion of unreacted C$_3$ hydrocarbons. The IPA stream is recycled to the etherification zone.

The operating conditions of the olefin hydration and etherification process herein are not especially critical and include a temperature of from about 60° to 450° C., preferably from about 90° to about 220° C. and most preferably from about 120° to about 200° C., a pressure of from about 100 to about 3500 psi, preferably from about 500 to about 2000 psi, a water to olefin mole ratio of from about 0.1 to about 30, preferably from about 0.2 to about 15 and most preferably from about 0.3 to about 3.

The olefin hydration process can be carried out under dense phase, liquid phase, vapor phase or mixed vapor-liquid phase conditions in batch or continuous manner using a stirred tank reactor or fixed bed flow reactor, e.g., trickle-bed, liquid-up-flow, liquid-down-flow, counter-current, co-current, etc. A liquid hourly space velocity (LHSV) of from about 0.1 to about 20, preferably about 0.1-2, when operating continuously is suitable.

The catalyst employed in the olefin hydration and etherification operations is acidic resin catalyst such as sulfonated polystyrene. Also, shape-selective acidic zeolite catalyst can be used. In general, the useful catalysts embrace two categories of zeolite, namely, the intermediate pore size variety as represented, for example, by ZSM-5, which possess a Constraint Index of greater than about 2 and the large pore variety as represented, for example, by zeolites Y, Beta and ZSM-12, which possess a Constraint Index no greater than about 2. Preferred catalysts include Zeolite Beta, Zeolite Y, ZSM-12, ZSM-5 and ZSM-35. Both varieties of zeolites will possess a framework silica-to-alumina ratio of greater than about 7.

For purposes of this invention, the term "zeolite" is meant to include the class of porotectosilicates, i.e., porous crystalline silicates, which contain silicon and oxygen atoms as the major components. Other components can be present in minor amounts, usually less than 14 mole %, and preferably less than 4 mole %. These components include aluminum, gallium, iron, boron, and the like, with aluminum being preferred. The minor components can be present separately or in mixtures in the catalyst. They can also be present intrinsically in the framework structure of the catalyst. The framework silica-to-alumina mole ratio referred to can be determined by conventional analysis. This ratio is meant to represent, as closely as possible, the mole ratio of silica to alumina in the rigid anionic framework of the zeolite crystal and to exclude any alumina which may be present in a binder material optionally associated with the zeolite or present in cationic or other form within the channels of the zeolite. In addition, zeolites as otherwise characterized herein but which are substantially free of aluminum, i.e., having silica-to-alumina mole ratios up to and including infinity, are useful and can even be preferable in some cases.

A convenient measure of the extent to which a zeolite provides controlled access to molecules of varying sizes to its internal structure is the aforementioned Constraint Index of the zeolite. A zeolite which provides relatively restricted access to, and egress from, its internal structure is characterized by a relatively high value for the Constraint Index, i.e., above about 2. On the other hand, zeolites which provide relatively free access to the internal zeolitic structure have a relatively low value for the Constraint Index, i.e., about 2 or less. The method by which Constraint Index is determined is described fully in U.S. Pat. No. 4,016,218, to which reference is made for details of the method.

Constraint Index (CI) values for some zeolites which can be used in the process of this invention are described in the following table together with the temperature at which the test was made:

| Zeolite | Constraint Index (At Test Temperature, °C.) |
| --- | --- |
| ZSM-4 | 0.5 (316) |
| ZSM-5 | 6–8.3 (371–316) |
| ZSM-11 | 5–8.7 (371–316) |
| ZSM-12 | 2.3 (316) |
| ZSM-20 | 0.5 (371) |
| ZSM-35 | 4.5 (454) |
| ZSM-48 | 3.5 (538) |
| ZSM-50 | 2.1 (427) |
| TMA Offretite | 3.7 (316) |
| TEA Mordenite | 0.4 (316) |
| Clinoptilolite | 3.4 (510) |
| Mordenite | 0.5 (316) |
| REY | 0.4 (316) |
| Amorphous Silica-Alumina | 0.6 (538) |
| Dealuminized Y | 0.5 (510) |
| Zeolite Beta | 0.6–2.0 (316–399) |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables, such as crystal size of the zeolite, the presence of occluded contaminants, etc., can affect the Constraint Index. Therefore, it will be appreciated that it may be possible to so select test conditions, e.g., temperatures, as to establish more than one value for the Constraint Index of a particular zeolite. This explains the range of Constraint Indices for zeolite Beta.

Useful zeolite catalysts of the intermediate pore size variety, and possessing a Constraint Index of greater than about 2 up to about 12, include such materials as ZSM-5, ZSM-11, ZSM-23, ZSM-35, and ZSM-38.

ZSM-5 is more particularly described in U.S. Pat. No. Reissue 28,341 (of original U.S. Pat. No. 3,702,886), the entire contents of which are incorporated herein by reference.

ZSM-11 is more particularly described in U.S. Pat. No. 3,709,979, the entire contents of which are incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference. Although ZSM-38 possesses a Constraint Index of 2.0, it is often classified with the intermediate pore size zeolites and will therefore be regarded as such for purposes of this invention.

The large pore zeolites which are useful as catalysts in the hydration and etherification step of the process of this invention, i.e., those zeolites having a Constraint Index of no greater than about 2, are well known to the art. Representative of these zeolites are zeolite Beta, zeolite X, zeolite L, zeolite Y, ultrastable zeolite Y (USY), dealuminized Y (Deal Y), rare earth-exchanged zeolite Y (REY), rare earth-exchanged dealuminized Y (RE Deal Y), mordenite, ZSM-3, ZSM-4, ZSM-12, ZSM-20, and ZSM-50 and mixtures of any of the foregoing. Although zeolite Beta has a Constraint Index of about 2 or less, it should be noted that this zeolite does not behave exactly like other large pore zeolites. However, zeolite Beta does satisfy the requirements for a catalyst of the present invention.

Zeolite Beta is described in U.S. Pat. No. Reissue 28,341 (of original U.S. Pat. No. 3,308,069), to which reference is made for details of this catalyst.

Zeolite X is described in U.S. Pat. No. 2,882,244, to which reference is made for the details of this catalyst.

Zeolite L is described in U.S. Pat. No. 3,216,789, to which reference is made for the details of this catalyst.

Zeolite Y is described in U.S. Pat. No. 3,130,007, to which reference is made for details of this catalyst.

Low sodium ultrastable zeolite Y (USY) is described in U.S. Pat. Nos. 3,293,192; 3,354,077; 3,375,065; 3,402,996,; 3,449,070; and 3,595,611, to which reference is made for details of this catalyst.

Dealuminized zeolite Y (Deal Y) can be prepared by the method found in U.S. Pat. No. 3,442,795, to which reference is made for details of this catalyst.

Zeolite ZSM-3 is described in U.S. Pat. No. 3,415,736, to which reference is made for details of this catalyst Zeolite ZSM-4 is described in U.S. Pat. No. 3,923,639, to which reference is made for details of this catalyst.

Zeolite ZSM-12 is described in U.S. Pat. No. 3,832,449, to which reference is made for the details of this catalyst.

Zeolite ZSM-20 is described in U.S. Pat. No. 3,972,983, to which reference is made for the details of this catalyst.

Zeolite ZSM-50 is described in U.S. Pat. No. 4,640,829, to which reference is made for details of this catalyst.

Also, included within the definition of the useful zeolites are crystalline porous silicoaluminophosphates such as those disclosed in U.S. Pat. No. 4,440,871, the catalytic behavior of which is similar to that of the aluminosilicate zeolites.

The zeolite(s) selected for use herein will generally possess an alpha value of at least about 1 and preferably at least 10. For the olefins hydration reaction, the most preferred alpha value for fresh catalyst is at least 400. "Alpha value", or "alpha number", is a measure of zeolite acidic functionality and is more fully described together with details of its measurement in U.S. Pat. No. 4,016,218, *J. Catalysis*, 6, pp. 278–287 (1966) and *J. Catalysis*, 61, pp. 390–396 (1980). Zeolites of low acidity (alpha values of less than about 200) can be achieved by a variety of techniques including (a) synthesizing a zeolite with a high silica/alumina ratio, (b) steaming, (c) steaming followed by dealuminization and (d) substituting framework aluminum with other species. For example, in the case of steaming, the zeolite(s) can be exposed to steam at elevated temperatures ranging from about 500° F. to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures employing elevated pressure, e.g., at from about 350° to about 700° F. with from about 10 to about 200 atmospheres. Specific details of several steaming procedures may be gained from the disclosures of U.S. Pat. Nos. 4,325,994; 4,374,296; and 4,418,235, the contents of which are incorporated by reference herein. Aside from, or in addition to any of the foregoing procedures, the surface acidity of the zeolite(s) can be eliminated or reduced by treatment with bulky reagents as described in U.S. Pat. No. 4,520,221, the contents of which are incorporated by reference herein.

In practicing the olefin hydration and etherification process step of the present invention, it can be advantageous to incorporate the zeolite(s) into some other material, i.e., a matrix or binder, which is resistant to the temperature and other conditions employed in the process. Useful matrix materials include both synthetic and naturally-occurring substances, e.g., inorganic materials such as clay, silica and/or metal oxides. Such materials can be either naturally-occurring or can be obtained as gelatinous precipitates or gels including mixtures of silica and metal oxides. Naturally-occurring clays which can be composited with the zeolite include those of the montmorillonite and kaolin families, which families include the sub-bentonites and the kaolins commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

In addition to the foregoing materials, the zeolite(s) employed herein can be composited with a porous matrix material such as carbon, alumina, titania, zirconia, silica, silica-alumina, silica-magnesia, silica-zirconia, silica-thoria, silica-beryllia, silica-titania, etc., as well as ternary oxide composition, such as silica-alumina-thoria, silica-alumina-zirconia, silica-alumina-magnesia, silica-magnesia-zirconia, etc.. The matrix can be in the form of a cogel. The relative proportions of zeolite component(s) and matrix material, on an anhydrous basis, can vary widely with the zeolite content ranging from between 1 to about 99 wt. %, and more usually in the range of about 5 to about 90 wt. % of the dry composite.

In some cases, it may be advantageous to provide the zeolite hydration etherification catalyst(s) in the form of an extrudate bound with a low acidity refractory oxide binder employing the method described in commonly assigned, copending U.S. patent application Ser. No. 44,639, filed May 1, 1987, the contents of which are incorporated by reference herein. In accordance with said method, zeolite, water and a low acidity refractory oxide binder, e.g., silica, which contains at least an extrusion-facilitating amount of the binder in a colloidal state and which is substantially free of added alkali metal base and/or basic salt, is formed into an extrudable mass, the mass is extruded and the resulting extrudate is dried and calcined.

The original cations associated with zeolite(s) utilized herein can be replaced by a wide variety of other cations according to techniques well known in the art, e.g., by ion-exchange. Typical replacing cations include hydrogen, ammonium, alkyl ammonium and metal cations, and their mixtures. Metal cations can also be introduced into the zeolite. In the case of metal cations, particular preference is given to metals of Groups IB to IVIII of the Periodic Table, including, by way of example, iron, nickel, cobalt, copper, zinc, palladium, calcium, chromium, tungsten, molybdenum, rare earth metals, etc. These metals can also be present in the form of their oxides.

A typical ion-exchange technique involves contacting the particular zeolite with a salt of the desired replacing cation. Although a wide variety of salts can be employed, particular preference is given to chlorides, nitrates and sulfates. Representative ion-exchange techniques are disclosed in a number of patents including U.S. Pat. Nos. 3,140,249; 3,140,251; and 3,140,253.

Following contact with a solution of the desired replacing cation, the zeolite is then preferably washed with water and dried at a temperature ranging from about 150° to about 600° F. and thereafter calcined in air or other inert gas at temperatures ranging from about 500° to about 1500° F. for periods of time ranging from about 1 to about 48 hours or more.

In the instant invention, unreacted $C_3$ olefins along with or without recovered IPA from the hydration zone are converted to gasoline, distillate or aromatics by the MOG, MOGD or M-2 Forming process in contact with metallosilicate zeolite-type catalyst such as ZSM-5. In the case of conversion to aromatics of the hydration zone effluent, paraffins in the effluent can also be converted to aromatics by the M-2 Forming process.

Recent developments in zeolite catalyst and hydrocarbon conversion processes have created interest in using oxygenates and olefinic feedstocks for producing $C_5+$ gasoline, diesel fuel, etc. In addition to the basic work derived from ZSM-5 type zeolite catalyst, a number of discoveries have contributed to the development of a new industrial process. This process has significance as a safe, environmentally acceptable technique for utilizing feedstocks that contain lower olefins, especially $C_2$–$C_5$ alkenes. In U.S. Pat. Nos. 3,960,978 and 4,021,502, Plank, Rosinski and Givens disclose conversion of $C_2$–$C_5$ olefins, alone or in admixture with paraffinic components into higher hydrocarbons over crystalline zeolites having controlled acidity. Garwood et al. have also contributed improved processing techniques in U.S. Pat. Nos. 4,150,062; 4,211,640; and 4,227,992. A fluidized bed process for converting light olefinic streams to gasoline, sometimes referred to as the Mobil olefin to Gasoline process (MOG), is described by Avidan et al. in U.S. patent application Ser. No. 006,407, filed 23 Jan. 1987. The above identified disclosures are incorporated herein by reference in their entirety. The conversion of paraffins and/or olefins to aromatics is described in U.S. Pat. Nos. 3,760,024 and 3,756,942 to Cattanach, U.S. Pat. No. 3,845,150 to Yan et al., U.S. Pat. No. 4,090,949 to Owen et al. These patents are also incorporated herein by reference in their entirety.

Operating details for the typical conversion of olefins to gasoline or distillate as incorporated in the embodiments of the present invention are disclosed in U.S. Pat. Nos. 4,456,779; 4,497,968 to Owen et al. and 4,433,185 to Tabak, which are also incorporated herein by reference in their entirety.

As described above for the $C_3$ olefin hydration and etherification reaction as conventionally practiced, the hydrocarbon feed comprising propene is fed to the etherification zone along with a fresh water feedstream directly to the reactor. In one embodiment of the instant invention it has been discovered that the fresh water feedstream can be fed to the high pressure separator which receives the effluent from the DIPE reactor. In the high pressure separator the fresh water feedstream extracts IPA from the effluent and an aqueous stream is withdrawn from the separator and recycled to the DIPE reactor. In this embodiment the water reactant for the etherification reaction is contained in the aqueous recycled stream which contains a significant portion of recycled IPA. In this way the need for downstream separation of IPA for recycle to the DIPE reactor is substantially reduced.

Referring now to FIG. 1, a flow diagram of a preferred integrated process of the present invention is presented. A $C_3$ hydrocarbon feed typically comprising propene and propane is fed 110 to a hydration and etherification reaction vessel 115 containing an acidic catalyst. In the etherification vessel the $C_3$ hydrocarbons react with water and IPA which has been recycled to the reactor through conduit 116 from a high pressure separator 120. The effluent 117 from the etherification zone contains DIPE, IPA, unreacted water, unreacted $C_3$ hydrocarbons and a minor amount of dimeric and trimeric addition products of propene. The effluent 117 from the reaction zone 115 is passed to the high pressure separator 120 in conjunction with a fresh water feedstream 118. In the high pressure separator the fresh water feed effectively extracts a portion of IPA from the effluent stream 117. The aqueous stream containing IPA is separated and pumped 119 through conduit 116 for recycle as previously noted. From the high pressure separator another stream containing DIPE, unextracted IPA, unreacted $C_3$ hydrocarbons is withdrawn 121 and optionally heated 122 to a temperature to effect the evaporation of a major portion of unreacted $C_3$ hydrocarbons in an optional high pressure flash evaporator 125. The $C_3$ hydrocarbon vapor 124 is withdrawn from the flash evaporator and all or a part of it is recycled 126 to etherification zone 115 through a cooler compressor system 127. Alternatively, all or a part of the $C_3$ hydrocarbons are passed 128 to an oxygenates and hydrocarbon conversion zone 129.

From the flash evaporator 125 a stream is withdrawn 130 containing a minor portion of unreacted $C_3$ hydrocarbons, a portion of IPA, and DIPE. This stream is separated in separator zone 131 to provide a DIPE product stream 132, a light hydrocarbon stream 133 comprising unreacted $C_3$ hydrocarbons and a stream 134 comprising IPA. The IPA stream 134 and stream 133 are passed to conversion zone 129 in conjunction with the flash evaporator vapor stream. A portion of stream 134 containing IPA can be recycled 135 to the DIPE reactor.

In the oxygenates and hydrocarbon zone 129 the streams separated from the DIPE etherification zone effluent and identified as a portion of stream 128 and 134 and stream 132 are contacted with metallosilicate catalyst, preferably ZSM-5, where, depending upon the conditions selected, these oxygenates and hydrocarbons are converted to higher molecular weight hydrocarbons comprising gasoline, gasoline and distillate or aromatics. Preferably, the conversion reaction is carried out with a conventional oxygenates and/or hydrocarbon feedstream 136, as described for the MOG, MOGD or M-2 Forming processes cited hereinbefore.

Continuing to refer to FIG. 1, in another embodiment of the invention, stream 121 from the high pressure separator is passed to separator 131 with processing in the high pressure flash evaporator 125. DIPE is recovered from separator 131. Unreacted $C_3$ and unextracted IPA are introduced to conversion zone 129 for conversion to $C_5+$ gasoline boiling range hydrocarbons; optionally in conjunction with fresh oxygenate and/or hydrocarbon feed to the 129 conversion zone.

From the foregoing description the advantages of the instant invention are clearly evident. The integration of the oxygenates and hydrocarbon conversion process with DIPE relieves the requirement to recycle unreacted $C_3$ hydrocarbons. This eliminates recompression costs associated with the recycle loop and also avoids the necessity of operating the DIPE reactor at higher pressures needed to maintain a satisfactory propene partial pressure. The unique process variation which extracts IPA in the high pressure separator also effectively relieves downstream IPA separation operations, to the benefit of overall process costs.

Figure 2:
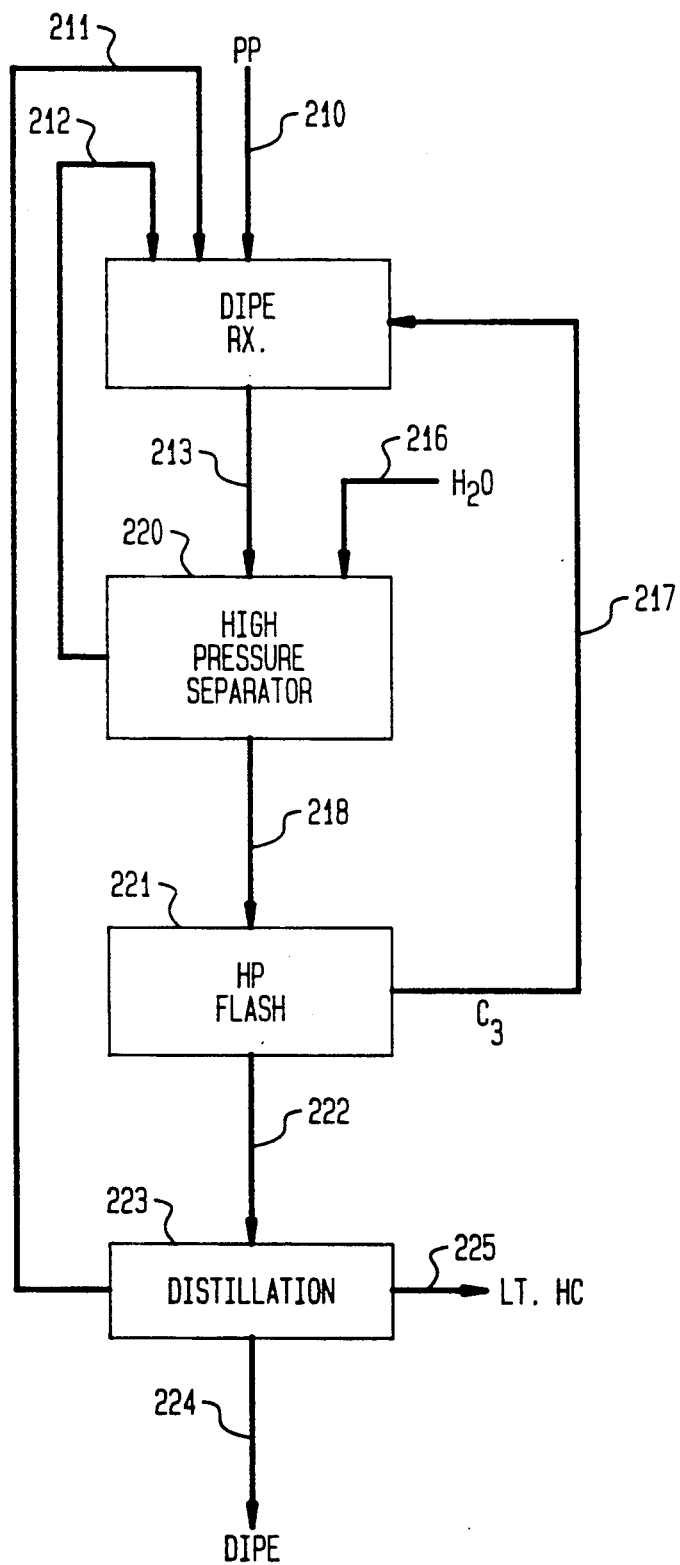
FIG. 2 is flow schematic illustrating the DIPE process incorporating the novel addition of feed water to the high pressure separator.

Referring now to FIG. 2, a schematic diagram is presented illustrating the novel variation of the DIPE process wherein IPA is extracted in a high pressure separator. $C_3$ hydrocarbon feedstock is passed 210 to DIPE olefin hydration and etherification reactor 215 containing acidic catalyst. The hydration and etherification reaction is carried out in vessel 215 in conjunction with recycled feedstreams 211 containing IPA, 212 containing IPA and water, and 217 containing unreacted $C_3$ hydrocarbons. The effluent from 215 is passed 213 to high pressure separator 220. The effluent, which contains DIPE, IPA and unreacted $C_3$ hydrocarbons is contacted by extraction with a fresh water feedstream 216 and the aqueous stream 212 is separated. From separator 220 a stream containing $C_3$ hydrocarbons, DIPE and IPA is passed 218 to a high pressure flash evaporator 221 from which a vapor stream comprising a major portion of unreacted $C_3$ hydrocarbons is separated and recycled 217 to vessel 215 after recompression. DIPE, IPA and a minor portion of $C_3$ and its oligomer hydrocarbons are passed 222 to separation section 223 for separation of DIPE 224, IPA recycled stream 211 and a light hydrocarbon stream 225 containing $C_3$ hydrocarbons.

While the invention has been described by specific examples and embodiments, there is no intent to limit the inventive concept except as set forth in the following claims.

What is claimed is:

1. An integrated process for the production of diisopropyl ether and $C_5+$ gasoline boiling range hydrocarbons, comprising:

contacting $C_3$ hydrocarbon feedstock and high pressure separator aqueous effluent recycle stream with acidic hydration and etherification catalyst in an etherification zone under etherification conditions to produce an effluent stream containing diisopropyl ether, isopropanol, unreacted water, unreacted $C_3$ hydrocarbons and higher olefinic hydrocarbons;

separating and extracting said effluent stream in a high pressure separation zone in contact with fresh water feedstream to produce said aqueous effluent recycle stream containing a portion of said isopropanol and unreacted water and a separation zone effluent stream containing diisopropyl ether, unextracted isopropanol, unreacted $C_3$ hydrocarbons and higher olefinic hydrocarbons;

heating and flashing said separator effluent stream at a temperature sufficient to further separate said separator effluent to produce a flash evaporator overhead vapor stream for compression and recycle to said etherification zone, said recycle stream containing a major portion of said unreacted $C_3$ hydrocarbons, and an evaporator bottom steam containing diisopropyl ether, unextracted isopropanol, a minor portion of said unreacted $C_3$ hydrocarbons and higher olefinic hydrocarbons;

separating said evaporator bottom stream to produce diisopropyl ether, a first stream containing $C_3$ hydrocarbons and a second stream containing isopropanol and higher olefinic hydrocarbons;

introducing said first and second stream to an oxygenates and hydrocarbons conversion zone in contact with acidic metallosilicate catalyst particles comprising shape-selective, medium pore, acid aluminosilicate zeolite under oxygenates and hydrocarbons conversion conditions whereby said evaporator bottom stream products comprising unreacted $C_3$ hydrocarbons, isopropanol and higher olefinic hydrocarbons are converted to higher molecular weight $C_5+$ gasoline boiling range hydrocarbons.

2. The process of claim 1 wherein said $C_3$ hydrocarbon feedstream comprises propene and propane.

3. The process of claim 1 wherein a portion of said evaporator overhead stream comprising said major portion of unreacted $C_3$ hydrocarbons is passed to said oxygenates and hydrocarbons conversion zone under oxygenates and hydrocarbons conversion conditions to produce higher molecular weight $C_5+$ hydrocarbons.

4. The process of claim 1 wherein a portion of said second stream is recycled to said etherification zone.

5. The process of claim 1 wherein a portion of said second stream is separated to recover isopropanol.

6. The process of claim 1 further comprising introducing a fresh oxygenates and/or hydrocarbons feedstream into said oxygenates and hydrocarbons conversion zone, said oxygenates and hydrocarbons taken from the group consisting essentially of methanol, ethanol, propanol, lower aldehydes, lower ethers, $C_2$–$C_6$ olefins and $C_2$–$C_6$ paraffins.

7. The process of claim 1 wherein said zeolite comprises ZSM-5.

8. The process of claim 1 wherein said oxygenates and hydrocarbons conversion conditions comprise olefin to gasoline conversion conditions.

9. The process of claim 1 wherein said oxygenates and hydrocarbons conversion conditions comprise olefin to gasoline and distillate conversion conditions and said higher molecular weight $C_5+$ hydrocarbons comprise gasoline and distillate boiling range hydrocarbons.

10. The process of claim 1 wherein said oxygenates and hydrocarbons conversion conditions comprise olefin and paraffin conversion conditions and said higher molecular weight hydrocarbons comprise aromatics.

11. The process of claim 1 wherein said acidic hydration and etherification catalyst is taken from the group consisting essentially of ZSM-5, zeolite Beta and acidic resins.

12. The process of claim 1 wherein said evaporator bottom stream is separated by extraction and distillation.

13. An integrated process for the production of diisopropyl ether and $C_5+$ gasoline boiling range hydrocarbons, comprising;

contacting $C_3$ hydrocarbon feedstock rich in propene and water with acidic hydration and etherification catalyst in an etherification zone under etherification conditions to produce an effluent stream containing diisopropyl ether, isopropanol, unreacted water, unreacted $C_3$ hydrocarbons and higher olefinic hydrocarbons;

separating said effluent stream to produce an aqueous stream containing a portion of said isopropanol and an organic stream containing said unreacted $C_3$ hydrocarbons and diisopropyl ether;

separating said organic stream to recover diisopropyl ether and a stream containing said unreacted $C_3$ hydrocarbons;

introducing said stream containing unreacted $C_3$ hydrocarbons to an oxygenates and hydrocarbons conversion zone in contact with acidic metallosilicate catalyst particles comprising shape-selective, medium pore, acid aluminosilica zeolite under oxygenates and hydrocarbons conversion conditions to produce higher molecular weight $C_5+$ gasoline boiling range hydrocarbons.

14. The process of claim 13 wherein said second aqueous stream is recycled to said etherification zone.

15. The process of claim 13 wherein said organic stream contains isopropanol.

16. The process of claim 13 further comprising introducing a fresh oxygenates and/or hydrocarbons feedstream into said oxygenates and hydrocarbons conversion zone, said oxygenates and hydrocarbons taken from the group consisting essentially of methanol, ethanol, propanol, lower aldehydes, lower ethers, $C_2$–$C_6$ olefins and $C_2$–$C_6$ paraffins.

17. The process of claim 13 wherein said zeolite comprises ZSM-5.

18. The process of claim 13 wherein said oxygenates and hydrocarbons conversion conditions comprise olefin to gasoline conversion conditions.

19. The process of claim 13 wherein said oxygenates and hydrocarbons conversion conditions comprise olefin to gasoline and distillate conversion conditions and said higher molecular weight hydrocarbons comprise gasoline and distillate boiling range hydrocarbons.

20. The process of claim 13 wherein said oxygenates and hydrocarbons conversion conditions comprise olefin and paraffin conversion conditions and said higher molecular weight hydrocarbons comprise aromatics.

21. The process of claim 13 wherein said acidic hydration and etherification catalyst is taken from the group consisting essentially of ZSM-5, zeolite Beta and acidic resins.

22. A process for the production of diisopropyl ether, comprising;

contacting $C_3$ hydrocarbon feedstock rich in propene and high pressure separator aqueous effluent recycle stream with acidic hydration and etherification catalyst in an etherification zone under etherification conditions to produce an effluent stream containing diisopropyl ether, isopropanol, unreacted water, unreacted $C_3$ hydrocarbons and higher olefinic hydrocarbons;

separating said effluent stream in high pressure separator in contact with fresh water feedstream to produce said aqueous effluent recycle stream containing a portion of said isopropanol and said separator effluent stream containing diisopropyl ether, unextracted isopropanol, unreacted $C_3$ hydrocarbons and higher olefinic hydrocarbons;

separating said separator effluent stream to produce a vapor stream containing a major portion of said unreacted $C_3$ hydrocarbons and a steam containing diisopropyl ether, unextracted isopropanol, a minor portion of said unreacted $C_3$ hydrocarbons and higher olefinic hydrocarbons;

compressing and recycling a portion of said vapor stream to said etherification zone;

separating said stream containing diisopropyl ether to recover diisopropyl ether, a first stream containing $C_3$ hydrocarbons and a second stream containing isopropanol and higher olefinic hydrocarbons.

23. The process of claim 22 further comprising introducing said first and second streams containing unreacted $C_3$ hydrocarbons, isopropanol and higher olefinic hydrocarbons to an oxygenates and hydrocarbons conversion zone in contact with acidic metallosilicate catalyst particles under oxygenates and hydrocarbons conversion conditions to produce higher molecular weight $C_5+$ gasoline boiling range hydrocarbons.

24. The process of claim 22 wherein a portion of said vapor stream is passed to said conversion zone.

25. The process of claim 22 wherein said acidic hydration and etherification catalyst is taken from the group consisting essentially of ZSM-5, zeolite Beta and acidic resins.

* * * * *